(12) United States Patent
Bitossi et al.

(10) Patent No.: US 9,096,443 B2
(45) Date of Patent: Aug. 4, 2015

(54) MAGNETITE IN NANOPARTICULATE FORM

(75) Inventors: Marco Bitossi, Montelupo Fiorentino (IT); Giovanni Baldi, Montespertoli (IT); Franco Innocenti, Florence (IT)

(73) Assignee: Colorobbia Italia S.P.A., Sovigliana-Vinci (IT)

( * ) Notice: Subject to any disclaimer, the term of this patent is extended or adjusted under 35 U.S.C. 154(b) by 0 days.

(21) Appl. No.: 13/516,166

(22) PCT Filed: Dec. 15, 2010

(86) PCT No.: PCT/IB2010/055836
§ 371 (c)(1),
(2), (4) Date: Jun. 14, 2012

(87) PCT Pub. No.: WO2011/073922
PCT Pub. Date: Jun. 23, 2011

(65) Prior Publication Data
US 2012/0251437 A1  Oct. 4, 2012

(30) Foreign Application Priority Data

Dec. 15, 2009  (IT) ................................ FI2009A0258

(51) Int. Cl.
*C01G 49/08* (2006.01)
*A61K 33/26* (2006.01)
*A61K 41/00* (2006.01)
*B82Y 30/00* (2011.01)

(52) U.S. Cl.
CPC ............... *C01G 49/08* (2013.01); *A61K 33/26* (2013.01); *A61K 41/0052* (2013.01); *B82Y 30/00* (2013.01); *C01P 2004/64* (2013.01); *C01P 2006/42* (2013.01)

(58) Field of Classification Search
CPC ..................................................... C01G 49/08
USPC ................... 423/632, 633, 634; 252/62.56
See application file for complete search history.

(56) References Cited

U.S. PATENT DOCUMENTS

| 4,792,349 A * | 12/1988 | Trimm et al. ...................... 71/31 |
| 2009/0108229 A1 * | 4/2009 | Silverman et al. .......... 252/62.56 |
| 2011/0318261 A1 * | 12/2011 | Peng et al. ..................... 423/632 |

FOREIGN PATENT DOCUMENTS

| DE | 102004035803 A1 | 3/2005 |
| JP | 2008-110889 A | 5/2008 |
| WO | 03/081612 A1 | 10/2003 |
| WO | 2008/074804 A2 | 6/2008 |

OTHER PUBLICATIONS

Qian Yitai et al: "Hydrothermal Preparation and Characterization of Ultrafine Magnetite Powders," Materials Research Bulletin, Sep. 1, 1994, pp. 953-957, vol. 29, No. 9, Elsevier, Kidlington, GB.
S. Laurent et al.: "Iron Oxide Based MR Contrast Agents: from Chemistry to Cell Labeling," Current Medicinal Chemistry, Nov. 2009, pp. 4712-4727, vol. 16.
PCT; International Preliminary Report on Patentability dated Apr. 19, 2012 in Application No. PCT/IB2010/055836.
PCT; Written Opinion of the International Search Authority dated Mar. 24, 2011 in Application No. PCT/IB2010/055836.
Biao Liu et al., "Study on Preparing Fe3 O4 Nanoparticles by Polyol Process", Chemical Engineering, vol. 35, No. 7, pp. 56-57 and 70 (English abstract).

* cited by examiner

*Primary Examiner* — Kaj K Olsen
*Assistant Examiner* — James Fiorito
(74) *Attorney, Agent, or Firm* — LeClairRyan, a Professional Corporation

(57) ABSTRACT

The present invention relates to a process for the polyol-type synthesis of nanoparticulate magnetite starting from mixtures of $Fe^0$ and $Fe1^{III}$ in the presence of a mineral acid. The magnetite particles obtainable from the process have uniform size characteristics and have even presented higher SAR (Specific Absorption Rate) values than those of magnetosomes.

7 Claims, 1 Drawing Sheet

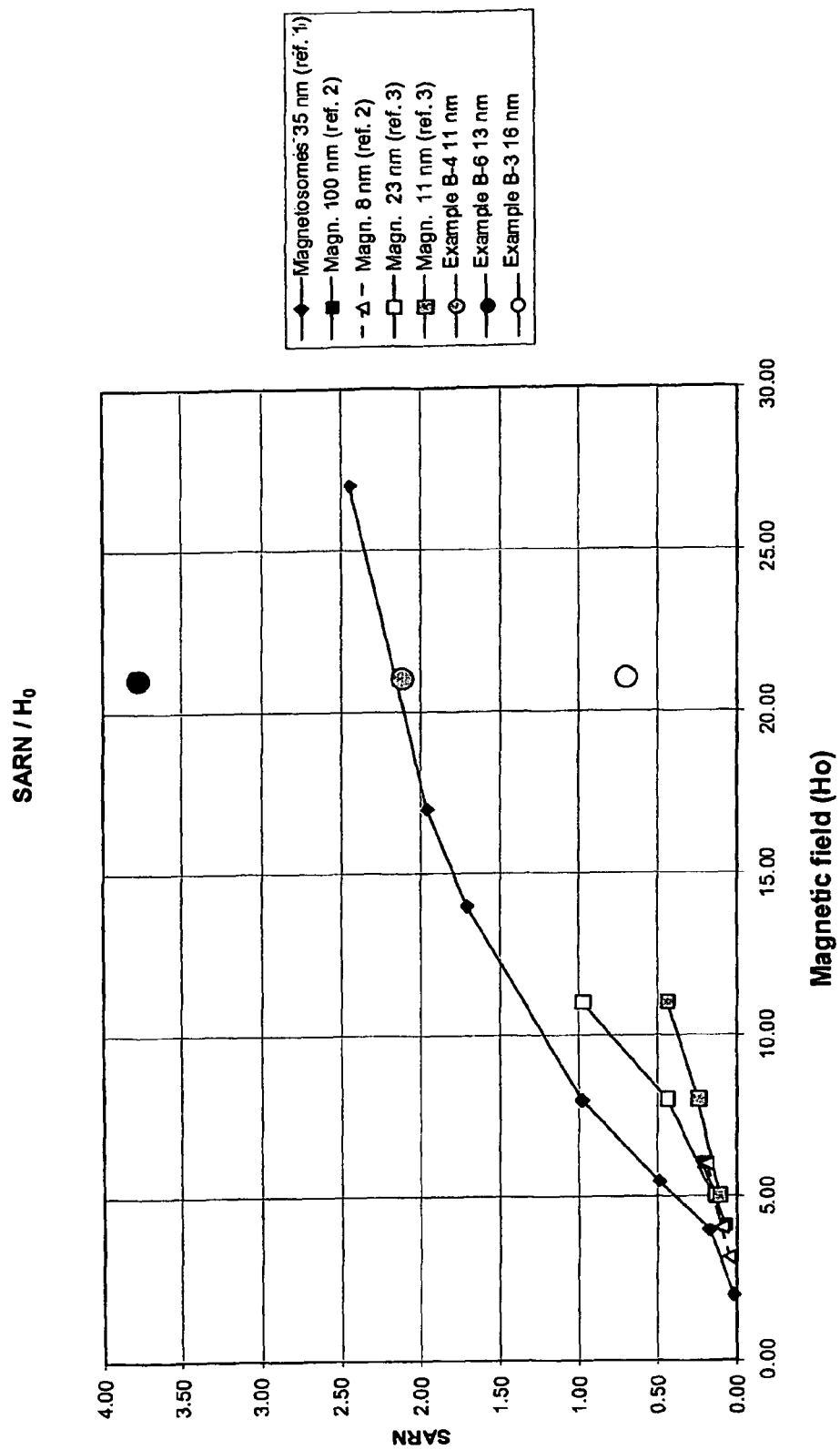

MAGNETITE IN NANOPARTICULATE FORM

FIELD OF THE INVENTION

The present invention relates to the field of processes for preparing magnetite in nanoparticulate form.

STATE OF THE ART

Magnetite is a mineral with ferromagnetic properties the chemical formula of which is $Fe_3O_4$. The formula for magnetite can also be written as $FeO.Fe_2O_3$. Magnetite in nanoparticulate form, i.e. with size ranging from a few nanometers to some tens of nanometers, when immersed in a magnetic field in the radio wave range, is known to heat up and then release thermal energy to its surroundings hence giving rise to what is known as a hyperthermic effect or magnetic hyperthermia.

In oncology, hyperthermia is utilized to improve the effectiveness of chemotherapy or radiotherapy and in this respect, raising the temperature of a solid tumour to between 41 and 45° C. induces apoptosis of cancer cells. To achieve this end, magnetic nanoparticles can be employed by being brought into contact with the tumour to utilize their hyperthermic effect.

Thus, for example, biocompatible nanohybrids comprising a nanoparticulate magnetite core and a polymer or protein coating, possibly loaded with drugs and decorated with suitable targeting agents, are potential theranostic agents in which the capacity to develop heat under the effect of an EM field (hyperthermic effect), the drug delivery and the capacity to be detected during its action with imaging techniques (MRI) are synergistically combined.

Normally the hyperthermia values are expressed as SAR (Specific Absorption Rate) which is a value dependent both on the intensity of the magnetic field applied and the field inversion frequency according to the equation:

$$SAR = K * f(d) * F * f(H_0)$$

in which:
K=constant
F=field inversion frequency
f(d)=variable function related to crystallite size
$f(H_0)$=variable function related to the intensity of the applied magnetic field (according to some authors, approximating to $H_0^2$-$H_0^3$).

To exert a hyperthermic effect which is effective in oncology, biocompatible nanoparticles must have high SAR levels: biocompatible nanoparticles are firstly located within the tumour and then excited by an alternating magnetic field of moderate amplitude $H_0$ (12-25 mT) at a frequency F within the range 100-400 kHz [P. Wust, U. Gneveckow, M. Johannsen, D. Bohmer, T. Henkel, F. Kahmann, J. Sehouli, R. Felix, J. Ricke, A. Jordan, Int. J. Hyperthermia 22, 673 (2006)].

R. Hergt and S. Dutz in J. Magn. Magn. Mater. 311, 187 (2007) have estimated that biocompatible nanoparticles with a SAR higher than 1 kW/g could effectively treat tumours 3 mm in diameter.

Hitherto, the most widely studied materials for magnetic hyperthermia have been iron oxides because of their total biocompatibility and their relative simplicity of synthesis. In the literature, the most efficient magnetite obtained by synthesis has presented SAR values up to 0.6 W/g at 400 kHz (R. Hergt, R. Hiergeist, I. Hilger, W. A. Kaiser, Y. Lapatnikov, S. Marge) and U. Richter, J. Magn. Magn. Mater. 270, 345 (2004)).

Currently, magnetosomes (magnetite crystals present in certain animal cells) are considered the most efficient magnetic structures from the hyperthermia viewpoint for biomedical applications (R. Hergt, R. Hiergeist, M. Zeisberger, D. Schüler, U. Heyen, I. Hilger, W. A. Kaiser, J. Magn. Magn. Mater., 2005, 293, 80).

Magnetite synthesis in nanoparticulate form is widely described in the literature and in many patents.

The methods used can be classified into 3 main groups, namely:

1) Alkalization of solutions (aqueous or in polyalcohols) containing $Fe^{II}$ and $Fe^{III}$ ions in a 1:2 stoichiometric ratio;

2) Polyol-type synthesis in which $Fe^{II}$ and $Fe^{III}$ mixtures are again used in a 1:2 stoichiometric ratio;

3) Decomposition of iron compounds (inorganic or organic) in the presence of agents (such as oleic acid) which act both as reducers and as stabilizing agents.

All the described syntheses present considerable drawbacks when their practical application is assessed.

1) The alkalization method produces aggregated particles, which easily form precipitates, of poorly controlled size and low hyperthermia.

2) The "polyol synthesis" requires careful control of the stoichiometric ratio and usage of $Fe^{II}$ acetate, a raw material which is difficult to obtain, costly and difficult to store (it being strongly hygroscopic and extremely sensitive to oxidation).

3) Reductive synthesis with oleic acid and the like results in the formation of particles the surface of which is functionalized with lyophilic groups and hence insoluble in an aqueous environment.

The particles obtained in cases 2 and 3, however, also have low SAR values when compared to the values presented by magnetosomes.

There is therefore an evident need to provide a process enabling magnetite to be obtained in nanoparticulate form which has sufficiently high SAR values enabling it to be used for magnetic hyperthermia in the biomedical field.

DEFINITIONS AND ABBREVIATIONS

SAR=specific absorption rate

SARN=normalized SAR with respect to the frequency of field inversion

The term "nanoparticles" means particles between 1 and 100 nm in size.

A polyalcohol solvent is an alcohol, such as glycerol, which contains two or more alcohol functions and has a boiling point above 250° C. and a melting point above 0° C.

SUMMARY OF THE INVENTION

The present invention resolves the aforesaid problems by means of a polyol-type process in which magnetite nanoparticles are obtained, said process comprising a step (ii) in which said nanoparticles are prepared in a polyalcohol solvent starting from metallic iron and $Fe^{III}$ in the presence of a catalyst and a suitable amount of water.

The process of the invention enables magnetite nanoparticles of uniform and controlled size thus presenting high hyperthermic efficiency. The process according to the invention is easy and efficient and allows avoiding the use of $Fe^{II}$ salts which present the aforedescribed drawbacks.

BRIEF DESCRIPTION OF THE FIGURES

FIG. 1 shows a graph relating to tables 1-5 where the y-axis indicates the SARN values and the x-axis indicates the values for the applied magnetic field amplitude.

DETAILED DESCRIPTION OF THE INVENTION

The process of the invention is preferably carried out starting from $Fe^0$ by means of the following steps:
i) preparation of a polyalcohol solution of $Fe^{III}$ starting from $Fe^0$;
ii) polyol-type preparation of the magnetite nanoparticles by means of the process of the invention as aforedescribed in which the solution obtained from step (i) is used as the source of $Fe^{III}$.

The above step (i) is none other than the well-known and well-described reaction of acid attack (even weak acids such as acetic acid) on iron in accordance with the equation:

$$Fe^0 + 2H^+ \rightarrow Fe^{2+} + 2H_2\uparrow \quad (1)$$

In the literature the reaction is normally described in an aqueous environment, but it has now been found that it can also be carried out under "polyol synthesis" conditions while maintaining the environment devoid of oxidants (such as atmospheric oxygen).

The $Fe^{II}$ solution in polyalcohols can subsequently be completely oxidized to $Fe^{III}$ (for instance, acetate) by bubbling air in the reaction medium with at a temperature less than 100° C.

Hence in a preferred form, in step (i) the process of the invention involves the preparation of a polyalcohol solution of $Fe^{III}$ means of the following steps:
a) preparing a $Fe^{II}$ solution starting from $Fe^0$ in a polyalcohol solvent and in the presence of an organic acid;
b) preparing a $Fe^{III}$ solution by bubbling air into the solution obtained from step a) then filtering off any residual metallic iron.

Preferably step a) is conducted at a temperature between 130 and 200° C. while step b) is conducted at a temperature of less than 100° C.

Said organic acid is preferably chosen from acids that form $Fe^{II}$ compounds which are soluble in a polyalcohol solvent, in particular acetic acid, propionic acid, lactic acid, glycolic acid.

Preferably in step a) the acid is used in a molar amount equal to 4-5 times the moles of metallic Fe.

Preferably, for step a) the metallic Fe is suspended in an amount by weight of polyalcohol equal to 80-120 times the $Fe^0$ weight.

The aforesaid step (ii) is the step in which a mixture of $Fe^0$ and $Fe^{III}$ ions in polyalcohol solvent is heated in the presence of a suitable amount of water and in the presence of an acid catalyst.

It has been discovered that under "polyol synthesis" conditions (solvent is a polyalcohol such as glycerine or propylene glycol or diethylene glycol, at a temperature preferably comprised between 130 and 200° C.), when a suitable catalyst is present, the iron (III) is reduced by the metallic iron in accordance with the following equation:

$$2Fe^{3+} + Fe^0 \rightarrow 3Fe^{2+} \quad (2)$$

The $Fe^{II}$ formation reaction is catalyzed by an acid environment. In particular mineral acids such as hydrochloric acid or sulphuric acid, or salts that exhibit acid hydrolysis such as iron chloride ($FeCl_3$) can be used as catalysts.

Since the kinetics of a redox reaction (2) is relatively slow whereas the formation of magnetite from $Fe^{II}$ and $Fe^{III}$ under the chosen temperature conditions is rapid, the iron (II) that forms reacts completely with the excess Fe(III) present to form magnetite in accordance with the equation:

$$2Fe^{3+} + Fe^{2+} + 4H_2O \rightarrow Fe_3O_4 + 8H^+ \quad (3)$$

The complete reaction for magnetite formation can hence be described as:

$$8Fe^{3+} + Fe^0 + 12H_2O \rightarrow 3Fe_3O_4 + 24H^+ \quad (4)$$

In accordance with the invention, nanoparticulate magnetite can preferably be prepared in solvents such as glycerine, propylene glycol, diethylene glycol and all analogous polyalcohols, conveniently at a temperature between 130 and 200° C. The amount of water in the solvent is a key factor in controlling the size of the hydrodynamic radius of the magnetic nanoparticles obtained, measured by DLS (dynamic light scattering); the size of the magnetite crystallites is in fact determined from the operating concentration and from the concentration of the water present in the reaction environment.

Preferably the water is present in a molar amount equal to 1.5-5 times the moles of $Fe^{III}$ salt used in step (ii).

Preferably the $Fe^0$ is present in a molar amount equal to 0.2-1 time the moles of $Fe^{III}$ salt used in step (ii).

Preferably, for step (ii) the metallic Fe is suspended in an amount by weight of polyalcohol equal to 0.5-4 times the $Fe^{III}$ solution weight.

It was also noted that by operating in a semi-continuous manner by making consecutive additions of the $Fe^{III}$ solution (or alternatively $Fe^{III}$ acetate or other salts soluble in a glycolic solvent), i.e. in a manner such that the magnetite formation reaction takes place in consecutive steps, higher hyperthermic efficiency values could be attained (see examples B3-B6: methods for measuring hyperthermic effect are given in the experimental part). A similarly convenient method is to control the addition rate of the $Fe^{III}$ solution such that the temperature does not undergo substantial variations (i.e. remains stable, with $\Delta T < 10°$ C.) during the addition (see examples B-5 and B-6).

Preferably the $Fe^{III}$ is added in the form of a polyalcohol solution at a concentration of 2-5 wt %.

Preferably the acid catalyst is used in molar amounts equal to 0.01-0.1 times the moles of the $Fe^{III}$ salt used in step (ii).

At the end of step (ii) the solid residue (metallic iron) is separated from the liquid phase by filtration to obtain a clear dark brown product (containing the magnetite in nanoparticulate form) which exhibits marked magnetic properties.

The SAR values found for the nanoparticles obtained by the process of the invention were, for the same frequency and intensity of the applied magnetic field, comparable with or higher than those known and reported in the literature for magnetosomes (see tables 1-5 and FIG. 1).

Synthetically obtained magnetite nanoparticles with said magnetic hyperthermia properties have no precedents in the literature; the hyperthermic effect observed is due to a specific and high degree of crystallinity in the structure of the magnetite obtained by the process of the invention.

The magnetite obtained by the aforedescribed process is potentially useful for preparing theranostic compositions for the hyperthermic and/or diagnostic treatment (by MRI) of tumours.

For biomedical applications it is of particular importance that the magnetite nanoparticles are stable in a physiological environment i.e. in an aqueous environment, and in the presence of relatively high salinity. The nanoparticulate magnetite obtained according to the present invention can easily be rendered stably dispersible in water by treating the reaction product (4) with phosphoric acid. In this manner, a solid precipitate is obtained by centrifugation which (after washing with water to remove excess phosphoric acid) can easily be solubilized in diluted ammonia solution to obtain a slightly alkaline final pH of the dispersion. The present invention can be better understood in the light of the following working examples.

EXPERIMENTAL PART

A) Preparation of the Iron III Acetate Solution

Example A-1

The following are introduced into a 500 ml flask equipped with dropping funnel, thermometer, cooler and system for flushing with gas:

| Reagent | Quantity (g) | Content |
|---|---|---|
| DEG | 150.00 | >99% |
| Metallic Fe | 1.50 | 99% |
| Acetic acid | 8.00 | 99% |

The system is firstly fluxed with nitrogen and then (still under inert gas) heating is commenced, setting the temperature at 150° C. After 12 hours the almost complete disappearance of the metallic base iron and a colour change in the solution can be noted.

While maintaining the system under nitrogen the temperature is lowered to 85° C., after which air bubbling is started. A colour change in the solution is immediately noted, it becoming dark red in colour. Air bubbling is maintained for 2 hours then the system is cooled to ambient temperature.

The solution is filtered through a buchner funnel to remove residual iron traces after which the solution can be used in the subsequent steps.

B) Preparation of the Magnetite

Example B-1

The following are introduced into a 500 ml flask equipped with dropping funnel, thermometer, cooler and nitrogen inerting system:

| Reagent | Quantity (g) | Content |
|---|---|---|
| DEG | 150.00 | >99% |
| H$_2$O | 1.50 | 100% |

The following is added at a temperature of 150° C.:

| | | |
|---|---|---|
| Fe$_{metal}$ | 1.50 | 99% |

Immediately followed by:

| | | |
|---|---|---|
| Fe(CH$_3$COO)$_3$ $_{solution}$ in DEG | 30.00 | 4.34% |

The temperature drops to below 140° C. (138° C.) and is then returned to 150° C. and maintained thereat for 25 minutes. The following is then added:

| | | |
|---|---|---|
| 32% HCl | 0.10 | 32.00% |

The temperature is brought to 160° C. and maintained thereat for 3 hours. At the end of this time, the liquid phase is separated from the metallic iron residue. A black-brown solution is obtained with marked magnetic properties.

Size analysis using DLS (Dynamic Light Scattering): PDI: 0.230; average Z: 15.86 nm; Mean volume 11.43 nm; Peak percentage 99.9%.

Magnetite content (ICP) : 2650 ppm
Theoretical Magnetite content: 0.26%
30 sec. Hyperthermia: 0.6° C.
Specific hyperthermia 1% : 2.4° C.

Example B-2

The following are introduced into a 500 ml flask equipped with dropping funnel, thermometer, cooler and nitrogen inerting system:

| Reagent | Quantity (g) | Content |
|---|---|---|
| DEG | 150.00 | >99% |
| H$_2$O | 1.50 | 100% |

The T is set at 150° C. As soon as this temperature has been reached, the following is added:

| | | |
|---|---|---|
| Fe$_{metal}$ | 1.50 | 99% |

Immediately afterwards the following is slowly added drop-wise, ensuring that the temperature does not drop below 145° C.

| | | |
|---|---|---|
| Fe(CH$_3$COO)$_3$ $_{solution}$ in DEG | 120.00 | 4.34% |

The temperature is returned to 150° C. and maintained thereat for 25 minutes. The following is then added:

| | | |
|---|---|---|
| 32% HCl | 0.10 | 32.00% |

The temperature is brought to 170° C. and maintained thereat for 3 hours.

At the end of this time the liquid phase is separated from the metallic iron residue.

A black solution is obtained with marked magnetic properties.

Dynamic size analysis: PDI 0.130; Z 24.00; Mean volume 21.29 nm; Peak percentage 100%.

Magnetite content (I.C.P.): 0.70%
Theoretical magnetite content: 0.71%
30 sec. Hyperthermia: 4.2° C.
Specific hyperthermia 1%: 5.9° C.

Example B-3

The following are introduced into a 500 ml flask equipped with dropping funnel, thermometer, cooler and system for flushing with gas:

| Reagent | Quantity (g) | Content |
|---|---|---|
| DEG | 150.00 | >99% |
| H$_2$O | 1.50 | 100% |

The temperature is set at 150° C. As soon as this temperature has been reached, the following is added:

| | | |
|---|---|---|
| Fe$_{metal}$ | 1.50 | 99% |

Immediately followed by:

| | | |
|---|---|---|
| Fe(CH$_3$COO)$_3$ $_{solution}$ in DEG | 30.00 | 4.34% |

The temperature drops to 138° C. The temperature is returned to 150° C. and maintained thereat for 25 minutes. The following is then added:

| | | |
|---|---|---|
| 32% HCl | 0.10 | 32.00% |

The temperature is brought to 160° C. and maintained thereat for 30 minutes.
The following is then added:

| | | |
|---|---|---|
| Fe(CH$_3$COO)$_3$ $_{solution}$ in DEG | 30.00 | 4.34% |

The temperature is returned to 160° C. and maintained thereat for 45 minutes. The procedure is repeated three times for a TOTAL addition of 120 grams of solution.

The suspension is maintained at 160° C. for 1 hour then allowed to cool, still under inert gas.

At the end, the liquid phase is separated from the metallic iron residue. A black solution is obtained with marked magnetic properties.

Dynamic size analysis: PDI 0.074; Z 20.93; Mean volume 18.27 nm; Peak percentage 100%.
Magnetite content (I.C.P.): 0.74%
Theoretical magnetite content: 0.71%
30 sec. Hyperthermia: 8.4° C.
Specific hyperthermia 1%; 11.4° C.

Example B-4

The following are introduced into a 500 ml flask equipped with dropping funnel, thermometer, cooler and nitrogen inerting system:

| Reagent | Quantity (g) | Content |
|---|---|---|
| DEG | 150.00 | >99% |
| H$_2$O | 1.50 | 100% |

The temperature is set at 150° C. As soon as this temperature has been reached the following is added:

| | | |
|---|---|---|
| Fe$_{metal}$ | 1.50 | 99% |

Followed immediately afterwards by:

| | | |
|---|---|---|
| Fe(CH$_3$COO)$_3$ $_{solution}$ in DEG | 30.00 | 4.34% |

The temperature drops to 138° C. The temperature is returned to 150° C. and maintained thereat for 25 minutes. The following is then added:

| | | |
|---|---|---|
| 32% HCl | 0.10 | 32.00% |

The temperature is brought to 160° C. and maintained thereat for 30 minutes. The temperature is then raised to 170° C., this latter temperature being maintained for 30 minutes.
The following is then added:

| | | |
|---|---|---|
| Fe(CH$_3$COO)$_3$ $_{solution}$ in DEG | 30.00 | 4.34% |

The temperature is returned to 170° C. and maintained thereat for 45 minutes. The procedure is repeated five times for a TOTAL addition of 180 grams of solution.

The suspension is maintained at 170° C. for 1 hour then allowed to cool, still under inert gas.

At the end, the liquid phase is separated from the metallic iron residue. A black solution is obtained with marked magnetic properties.

Dynamic size analysis: PDI 0.051; Z 24.00; Mean volume 21.29 nm; Peak percentage 100%.
Magnetite content (I.C.P.): 0.86%
Theoretical magnetite content: 0.88%
30 sec Hyperthermia: 25.8° C.
Specific hyperthermia 1%: 29.3° C.

Example B-5

The following are introduced into a 1000 ml flask equipped with dropping funnel, thermometer, cooler and nitrogen inerting system:

| Reagent | Quantity (g) | Content |
|---|---|---|
| DEG | 300.00 | >99% |
| H$_2$O | 1.50 | 100% |
| Fe$_{metal}$ | 3.00 | 100% |

The temperature is set at 170° C. As soon as this temperature has been reached the following is added:

| | | |
|---|---|---|
| 32% HCl | 0.25 | 32.00% |

This temperature is maintained for 5 minutes after which the following is added:

| | |
|---|---|
| Fe(CH$_3$COO)$_3$ $_{solution}$ | 60.00 g |

The temperature drops as a result of this addition, the suspension is allowed to return to the set temperature (170° C.) then left under agitation at constant temperature.

After 40 minutes the following is slowly added drop-wise (100 g/h)

| | |
|---|---|
| Fe(CH$_3$COO)$_3$ $_{solution}$ | 480.00 g | and the temperature is monitored to ensure it always remains between 168 and 172° C. When the addition is completed the system is again maintained at 170° C. for a further 2 hours then cooled to ambient temperature after which the liquid phase is separated from the metallic iron residue. A black solution is obtained with marked magnetic properties.

Dynamic size analysis: PDI 0.030; Z 23.82; mean volume 21.43 nm; Peak percentage 100%.
Magnetite content (I.C.P.): 1.07%
Theoretical magnetite content: 1.04%
30 sec. Hyperthermia: 31.4° C.
Specific hyperthermia 1%: 29.35° C.

Example B-6

The following are introduced into a 1000 ml flask equipped with dropping funnel, thermometer, cooler and nitrogen inerting system:

| Reagent | Quantity (g) | Content |
|---|---|---|
| DEG | 300.00 | 99% |
| $H_2O$ | 1.50 | 100% |
| $Fe_{metal}$ | 3.00 | 100% |

The temperature is set at 170° C. As soon as this temperature is reached, the following is added:

| | | |
|---|---|---|
| 32% HCl | 0.25 | 32.00% |

This temperature is maintained for 5 minutes, after which time the following is added:

| | |
|---|---|
| $Fe(CH_3COO)_3$ solution | 60.00 g |

The temperature drops as a result of this addition, the suspension is allowed to return to the set temperature (170° C.) then left under agitation at constant temperature.

After 40 minutes the following is slowly added drop-wise (50 g/h)

| | |
|---|---|
| $Fe(CH_3COO)_3$ solution | 540.00 g | and the temperature is monitored to ensure it always remains between 168 and 172° C. When the addition is completed the system is again maintained at 170° C. for a further 2 hours then cooled to ambient temperature after which the liquid phase is separated from the metallic iron residue. A black solution is obtained with marked magnetic properties.

Dynamic size analysis: PDI 0.144; Z 47.78; Mean volume 38.67 nm; Peak percentage 100%.
Magnetite content (I.C.P.): 1.07%
Theoretical magnetite content: 1.07%
30 sec. Hyperthermia: 58.0° C.
Specific hyperthermia 1%: 54.20° C.

C) Solubilization of the Magnetite in Water

Example C-1

300 g of a 2% phosphoric acid solution in water is introduced into a 500 ml Erlenmeyer flask then 100 g of the solution of example B-6 is added under agitation.

The solution is maintained under agitation for 30 minutes, allowing the black flocculate which has formed to decant. The precipitate is separated magnetically and washed twice with demineralised water, each time maintaining the suspension under agitation for 20 minutes followed by decanting and magnetic separation.

The wet solid thus obtained is taken up with 200 g of 0.05 M ammonium hydroxide and left under agitation for 20 minutes. clear solution is obtained, presenting a dynamic size analysis comparable with the product of example B-6.

The product can be diluted in a phosphate-ammonia buffer at pH 7.4-7.8

D) Measurement of 30 sec. and Specific Hyperthermia. Calculation of SAR

To measure the hyperthermia data, we used Ameritherm Inc. solid state induction heating equipment, with the magnetic field $H_o$ set at 21 KA/m (kiloamperes/meter) and the frequency F set at 17 KHz (kilohertz).

The temperature increase measurements were undertaken at the centre of a 50 mm diameter coil on a sample (at ambient temperature, about 22° C.) of the suspension as obtained in the various examples described.

Immediately before the test, the temperature of the sample was measured, then the apparatus was activated for 30 seconds and the final temperature of the same sample was measured (30 sec. hyperthermia).

The measurement was undertaken on known sample volumes (0.5 ml); as the concentrations of the magnetic nanoparticles in the different samples are similar and assuming a linear dependence between the hyperthermic effect and concentration, it was possible to normalize the value obtained at a 1% concentration (specific hyperthermia) so as to obtain comparable values.

The hyperthermic efficiency of a material (Specific Absorption Rate—SAR) is defined as the total heat dissipated by the sample divided by the total mass of the absorbent phase and the irradiation time:

$$SAR = \frac{\sum_i Q_i}{m_{Ox} \cdot \Delta t_{rise}}$$

where i represents all the species involved in heat exchange and $m_{Ox}$ the total mass of the absorbent mass (in our case magnetite). As $Q_i = m_i \cdot C_{pi} \cdot \Delta T_i$ ($m_i$=mass of the species expressed in grams [g]; $C_p$=specific heat expressed in Joules/gram* degree [J/g*K]), the following is obtained:

$$SAR = \frac{\sum_i m_i C_{pi}}{m_{Oxide}} \cdot \Delta T / \Delta t$$

To minimize the contribution of heat exchange with the environment (since we operated in a non-temperature controlled environment) two strategies were used: to avoid any heat exchange at the start of irradiation, the samples were carefully conditioned at ambient temperature and (by determining the heating curve of the sample as a function of time) the slope of the curve at the zero point was extrapolated.

For each sample we separately considered the contribution of magnetite nanoparticles and of the matrix (essentially consisting of diethylene glycol) of which both the mass and specific heat capacity were known (0.67 J/g*K for magnetite and 2.4 J/g*K for diethylene glycol).

The method demonstrates good reproducibility with an estimated error of about 5%.

As an example, the sample of example B-4 presents the following parameters: Sample mass: 0.30 g Magnetite concentration: 0.86%

Total mass of diethylene glycol: 0.29742 g

Total mass of magnetite: 0.00258 g

Slope of the heating curve at point 0 (dT/dt): 1.293 K/s

From which the following is obtained:

Diethylene glycol: mass*specific heat= 0.29742*2.4=0.713808

Magnetite: mass*specific heat=0.00258*0.67=0.001729

Total heat capacity=0.713808 +0.001729=0.715537

Amount of absorbed heat=total heat capacity*dT/dt= 0.715537*1.293

SAR=amount of absorbed heat/total mass of magnetite

SAR=0.715537*1.270/0.00258

SAR=358.6

E) Comparison with Magnetosomes and Magnetite Obtained by Methods Known in the State of the Art As the SAR measurements undertaken on materials with hyperthermic effect are reported at different magnetic field and frequency values, and the $f(H_0)$ value is variable and not perfectly calculable, in order to compare the SARs of the different products with hyperthermic effect described in the literature, we used experiments on magnetosomes as a reference.

These are considered to be the most efficient magnetic structures from the hyperthermia viewpoint (see R. Hergt, R. Hiergeist, M. Zeisberger, D. Schüler, U. Heyen, I. Hilger, W. A. Kaiser, *J. Magn. Magn. Mater.*, 2005, 293, 80) and the SAR measurements were undertaken in a very wide magnetic field range.

To normalize the effects of the frequencies used (as the SAR is directly proportional to the applied frequency) we have defined a new SARN parameter, defined as SAR/F.

In the accompanying tables we report the SARN values for magnetosomes, for magnetites described in the literature and for magnetites synthesized by ourselves.

TABLE 1

Magnetosomes 36 nm (ref. 1)

| SAR | F (frequency) | $H_0$ (magnetic field) | SARN |
|---|---|---|---|
| 1000 | 410 | 27 | 2.44 |
| 800 | 410 | 17 | 1.95 |
| 700 | 410 | 14 | 1.71 |
| 400 | 410 | 8 | 0.98 |
| 200 | 410 | 5.5 | 0.49 |
| 70 | 410 | 4 | 0.17 |
| 8 | 410 | 2 | 0.02 |

TABLE 2

Magnetite 100 nm (ref. 2)

| SAR | F (frequency) | $H_0$ (magnetic field) | SARN |
|---|---|---|---|
| 88 | 410 | 6.02 | 0.21 |
| 58 | 410 | 5.00 | 0.14 |
| 32 | 410 | 4.12 | 0.08 |

TABLE 3

Magnetite 8 nm (ref. 2)

| SAR | F (frequency) | $H_0$ (magnetic field) | SARN |
|---|---|---|---|
| 78 | 410 | 6.03 | 0.19 |
| 40 | 410 | 4.07 | 0.10 |
| 20 | 410 | 3.16 | 0.05 |

TABLE 4

| SAR | F (frequency) | $H_0$ (magnetic field) | SARN |
|---|---|---|---|
| Magnetite 23 nm (ref. 3) | | | |
| 400 | 410 | 11.00 | 0.98 |
| 180 | 410 | 8.00 | 0.44 |
| 60 | 410 | 5.05 | 0.15 |
| Magnetite 11 nm (ref. 3) | | | |
| 180 | 410 | 11.00 | 0.98 |
| 100 | 410 | 8.00 | 0.44 |
| 45 | 410 | 5.03 | 0.15 |

TABLE 5

Synthesized magnetites

| Example | crystallite diameter (nm) | SAR | F (frequency) | $H_0$ (magnetic field) | SARN |
|---|---|---|---|---|---|
| B-4 | 11 | 359 | 170 | 21.00 | 2.11 |
| B-6 | 13 | 643 | 170 | 21.00 | 3.78 |
| B-3 | 16 | 119 | 170 | 21.00 | 0.70 |

[Ref. 1] R. Hergt, R. Hiergeist, M. Zeisberger, D. Schüler, U. Heyen, I. Hilger, W. A. Kaiser, *J. Magn. Magn. Mater.*, 2005, 293, 80.

[Ref. 2] R. Hiergeist, W. Andra, N. Buske, R. Hergt, I. Hilger, U. Richter, W. Kaiser, *J. Magn. Magn. Mater.*, 1999, 201, 420-422.

[Ref. 3] R. Hergt, R. Hiergeist, M. Zeisberger, G. Glöckl, W. Weitschies, L. P. Ramirez, I. Hilger, W. A. Kaiser, *J. Magn. Magn. Mater.*, 2004, 280, 358-368.

The invention claimed is:

1. A process for preparing magnetite nanoparticles, said process comprising a step (ii) wherein said nanoparticles are prepared from a mixture comprising a polyalcohol solvent, metallic iron, $Fe^{III}$ from a salt soluble in the polyalcohol solvent, a catalyst and a quantity of water in a molar amount equal to 1.5-5 times the moles of the salt.

2. Process according to claim 1 wherein said polyalcohol solvent is selected from the group consisting of glycerine, propylene glycol and ethylene glycol.

3. Process according to claim 1 wherein said catalyst is chosen from mineral acids.

4. Process according to claim 1 wherein the salt comprises iron acetate.

5. Process according to claim 1 wherein said $Fe^{III}$ salt is added to the mixture in the form of a polyalcohol solution.

6. Process according to claim 1 wherein said $Fe^{III}$ is added to the reaction mixture at a rate such that a temperature variation during the addition is less than 10° C.

7. Process according to claim 1 wherein step (ii) is preceded by a preparation step (i) of a polyalcohol solution of $Fe^{III}$ starting from $Fe^0$, wherein said step (i) comprises the following steps:

(a) preparing a $Fe^{II}$ solution starting from $Fe^0$ in a polyalcohol solvent and in the presence of an organic acid; and
(b) preparing a $Fe^{III}$ solution by bubbling air into the solution obtained from step (a).

* * * * *